(12) United States Patent
Ueda (10) Patent No.: US 8,618,519 B2
(45) Date of Patent: Dec. 31, 2013

(54) ENERGY DEGRADER AND CHARGED PARTICLE IRRADIATION SYSTEM INCLUDING THE SAME

(75) Inventor: Takamasa Ueda, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 39 days.

(21) Appl. No.: 13/455,754

(22) Filed: Apr. 25, 2012

(65) Prior Publication Data

US 2012/0267544 A1 Oct. 25, 2012

Related U.S. Application Data (63) Continuation of application No. PCT/JP2011/076440, filed on Nov. 16, 2011.

(30) Foreign Application Priority Data

Dec. 27, 2010 (JP) ................. P2010-289719

(51) Int. Cl.
*A61N 5/00* (2006.01)

(52) U.S. Cl.
USPC ............... 250/492.3; 250/492.1; 250/492.2; 250/396 R; 250/396 ML (58) Field of Classification Search
USPC ...... 250/492.1, 492.2, 492.3, 396 R, 396 ML
See application file for complete search history.

(56) References Cited

FOREIGN PATENT DOCUMENTS

| JP | H5-200126 A | 8/1993 |
|---|---|---|
| JP | H8-511978 A | 12/1996 |
| JP | H11-000408 A | 1/1999 |
| JP | 2000-354637 A | 12/2000 |

OTHER PUBLICATIONS

International Search Report for application No. PCT/JP2011/076440 dated Dec. 20, 2011.
English Translation of the International Preliminary Report on Patentability dated Jul. 11, 2013 corresponding to International Patent Application No. PCT/JP2011/076440.

*Primary Examiner* — Jack Berman
*Assistant Examiner* — Hanway Chang
(74) *Attorney, Agent, or Firm* — Squire Sanders (US) LLP (57) ABSTRACT

An energy degrader includes: an attenuation member that attenuates energy of entering charged particles to a different amount of energy according to an incident position of the charged particles; an energy adjustment drive unit that drives the attenuation member in a first axial direction in order to change the incident position of the charged particles; and a beam diameter adjustment drive unit that drives the attenuation member in a second axial direction different from the first axial direction in order to adjust the beam diameter of the charged particles.

5 Claims, 7 Drawing Sheets

ENERGY DEGRADER AND CHARGED PARTICLE IRRADIATION SYSTEM INCLUDING THE SAME

CROSS-REFERENCE TO RELATED APPLICATION

Priority is claimed to Japanese Patent Application No. 2010-289719, filed Dec. 27, 2010, and International Patent Application No. PCT/JP2011/076440, the entire content of each of which is incorporated herein by reference.

BACKGROUND

The present invention relates to an energy degrader that attenuates the energy of charged particles, and a charged particle irradiation system including the energy degrader.

DESCRIPTION OF THE RELATED ART

There is known equipment, such as a proton beam, that is used to perform cancer treatment by irradiating a patient with charged particles. This kind of equipment includes a cyclotron that accelerates charged particles generated by an ion source, a transport line through which the charged particles accelerated by the cyclotron are transported, and a rotatable irradiation device (rotating gantry) that irradiates a patient in a desired direction with the charged particles.

In a charged particle beam irradiation system described in the related art, a pair of attenuation members, which attenuate the energy of a charged-particle beam, is formed so as to have the shape of a wedge and is disposed so that the inclined surfaces of the wedge-shaped attenuation members face each other. The pair of attenuation members are movable forward and backward in one axial direction so as to move closer together or further apart from each other, and adjust the amount of energy attenuation by adjusting the thickness of the attenuation members through which the charged-particle beam passes.

SUMMARY

According to the invention, there is provided an energy degrader includes the attenuation member that attenuates energy of entering charged particles to a different amount of energy according to an incident position of the charged particles, an energy adjustment drive unit that drives the attenuation member in a first axial direction in order to change the incident position of the charged particles, and a beam diameter adjustment drive unit that drives the attenuation member in a second axial direction different from the first axial direction in order to adjust the beam diameter of the charged particles.

Further, according to the invention, there is provided an energy degrader includes the attenuation member that attenuates energy of entering charged particles to a different amount of energy according to an incident position of the charged particles, energy adjustment drive means for driving the attenuation member in a first axial direction in order to change the incident position of the charged particles, and a beam diameter adjustment drive means for driving the attenuation member in a second axial direction different from the first axial direction in order to adjust the beam diameter of the charged particles.

Further, according to the invention, there is provided a charged particle irradiation system that includes the energy degrader and performs the irradiation of the charged particles. The charged particle irradiation system includes an accelerator that accelerates the charged particles to be introduced into the energy degrader, and an irradiation device that performs the irradiation of the charged particles of which energy has been attenuated by the energy degrader.

The charged particle irradiation system according to the invention includes the energy degrader that attenuates the energy of entering charged particles. The energy degrader includes the attenuation member that attenuates energy of entering charged particles to a different amount of energy according to an incident position of the charged particles, an energy adjustment drive unit that drives the attenuation member in a first axial direction in order to change the incident position of the charged particles, and a beam diameter adjustment drive unit that drives the attenuation member in a second axial direction different from the first axial direction in order to adjust the beam diameter of the charged particles.

DETAILED DESCRIPTION

In the related art, a gap between the inclined surfaces of the attenuation members is increased on the path along which the charged-particle beam passes, when the attenuation members are separated from each other so that the length of the attenuation members through which a charged-particle beam passes is shortened in order to reduce the amount of attenuated energy of a charged-particle beam. When the gap between the inclined surfaces is increased, the length of the path along which a charged-particle beam passes through a space is increased and charged particles are diffused in the air. As a result, the beam diameter is increased.

It is desirable to provide an energy degrader that can adjust the amount of beam energy attenuation of charged particles and adjust the increase of the charged particle beam diameter (the scattering of a beam), as well as a charged particle irradiation system including the energy degrader.

In the energy degrader according to the invention, the attenuation member, which attenuates the energy of charged particles, is driven in the first axial direction by the energy adjustment drive unit. Accordingly, it is possible to change the incident position of the charged particles on the attenuation member and to adjust the amount of energy attenuation of the charged particles. Further, the energy degrader includes the beam diameter adjustment drive unit that drives the attenuation member in the second axial direction different from the first axial direction, and can adjust the length of the path of the charged particles, which have passed through the attenuation member, by changing the position of the attenuation member. Accordingly, it is possible to adjust the increase of the beam diameter of a charged-particle beam.

Furthermore, the energy degrader may further include a second attenuation member that is disposed on the upstream or downstream side of the attenuation member in a traveling direction of the charged particles and attenuates energy to a different amount of energy according to the incident position of the charged particles, and second energy adjustment drive unit that drives the second attenuation member in the first axial direction in order to change the incident position of the charged particles. Accordingly, the energy degrader includes the second attenuation member other than the attenuation member and reduces the gap between the attenuation member and the second attenuation member by driving only the attenuation member in the second axial direction. Therefore, it is possible to adjust the increase of the beam diameter of the charged-particle beam.

Moreover, the attenuation member may be disposed on the upstream side of the second attenuation member in the traveling direction of the charged particles. Accordingly, in order to reduce the gap between the attenuation member and the second attenuation member, only the attenuation member disposed on the upstream side need be driven in the second axial direction and the position of the second attenuation member, which is disposed on the downstream side, on the path of a beam does not need to be changed.

Further, the charged particle irradiation system according to the invention includes the energy degrader that attenuates the energy of entering charged particles. In the energy degrader, the attenuation member, which attenuates the energy of the charged particles, is driven in the first axial direction by the energy adjustment drive unit. Accordingly, it is possible to change the incident position of the charged particles on the attenuation member and to adjust the amount of attenuated energy of the charged particles. Further, the energy degrader includes the beam diameter adjustment drive unit that drives the attenuation member in the second axial direction different from the first axial direction, and can adjust the length of the path of the charged particles, which have passed through the attenuation member, by changing the position of the attenuation member. Accordingly, it is possible to adjust the increase of the beam diameter of a charged-particle beam. Furthermore, since it is possible to perform the irradiation of the charged particles of which the energy has been attenuated by the energy degrader, it is possible to adjust the irradiation depth at an object, which is to be irradiated, according to the energy of the charged particles.

Exemplary embodiments of an energy degrader according to the invention and a charged particle irradiation system including the energy degrader will be described below with reference to the drawings. A case where a charged particle irradiation system is a particle radiation therapy system will be described in this embodiment.

Charged Particle Irradiation System

A particle radiation therapy system is applied to, for example, cancer treatment, and is an apparatus that irradiates a tumor (irradiation target) in the body of a patient with a proton beam (charged particles).

Figure 1:
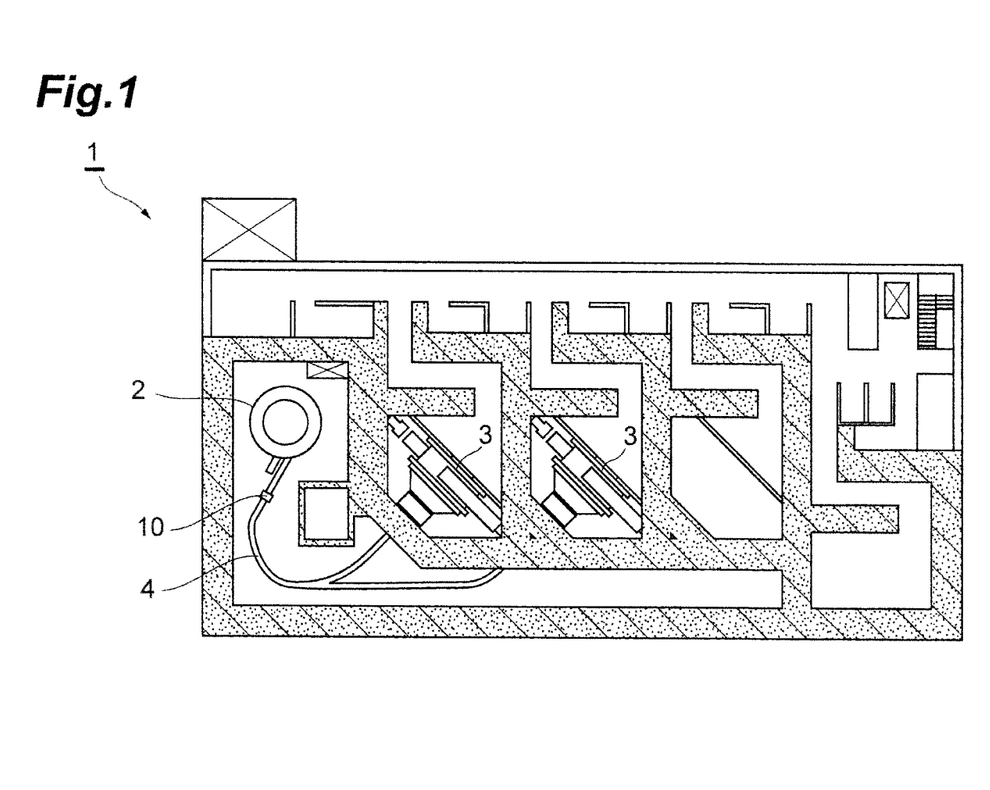
FIG. 1 is a view showing the disposition of a particle radiation therapy system according to an embodiment of the invention.

As shown in FIG. 1, a particle radiation therapy system 1 includes a cyclotron (particle accelerator) 2 that accelerates cations of hydrogen generated by an ion source (not shown) and takes out the anions of hydrogen as a proton beam, a rotatable rotating gantry (irradiation device) 3 that irradiates the patient with a proton beam in an arbitrary direction, and a transport line 4 through which a proton beam accelerated by the cyclotron 2 is transported to the rotating gantry 3.

The path of the proton beam accelerated by the cyclotron 2 is changed along the transport line 4, so that the proton beam is transported to the rotating gantry 3. The transport line 4 is provided with deflection magnets that change the path of the proton beam. Further, the transport line 4 is provided with an energy degrader 10 that attenuates the energy of the charged particles (details will be described below).

The rotating gantry 3 includes a treatment table on which a patient lies and an irradiation unit that irradiates the patient with a proton beam. Charged particles of which the energy has been attenuated by the energy degrader 10 are discharged from the irradiation unit to a target portion of the patient.

Energy Degrader

Figure 2:
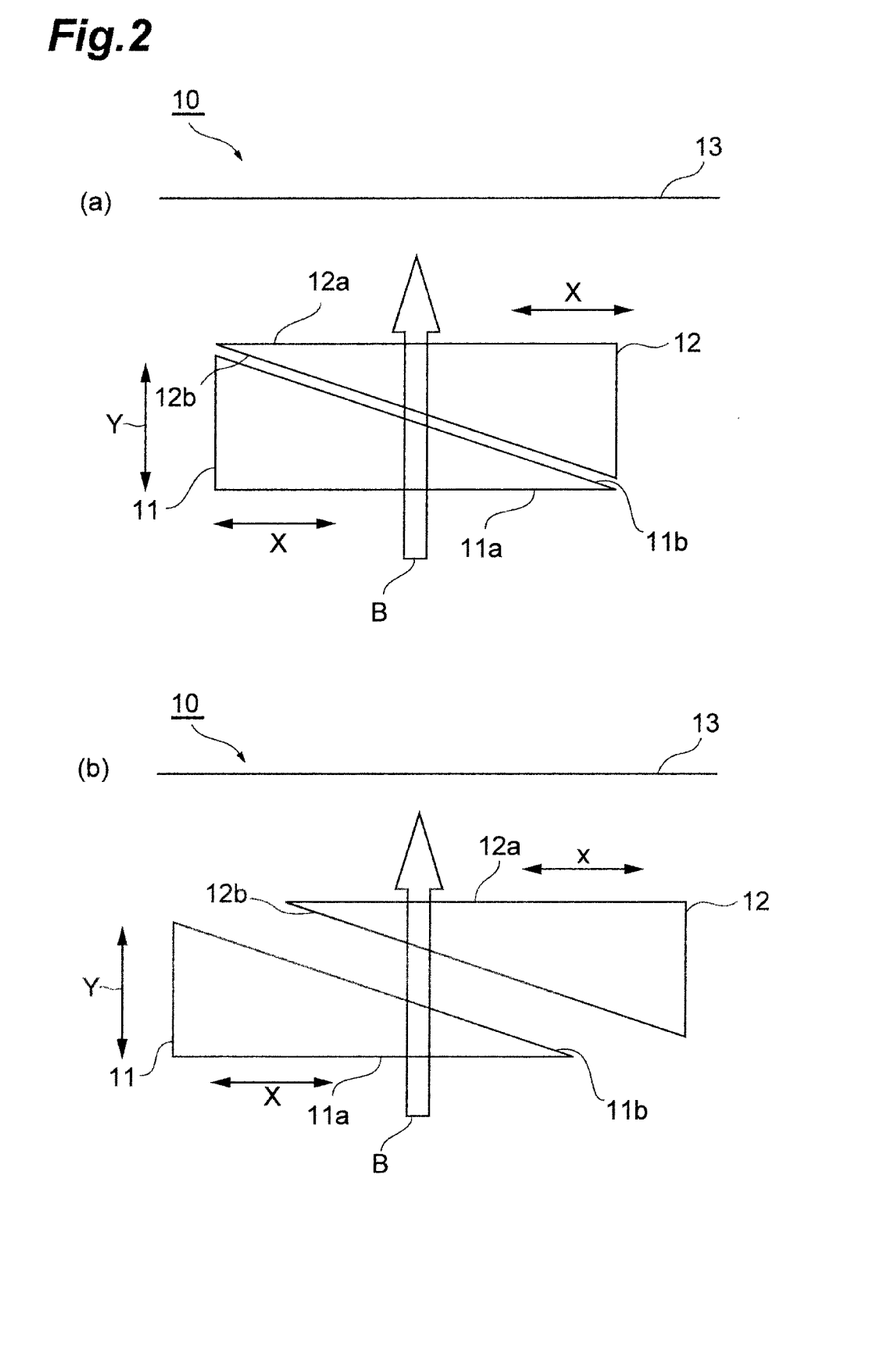
FIG. 2 is a schematic view showing an energy degrader according to an embodiment of the invention.

FIG. 2 is a schematic view showing the energy degrader according to the embodiment of the invention. The energy degrader 10 shown in FIG. 2 is provided on the path of a proton beam and attenuates the energy of the proton beam. The energy degrader 10 includes a pair of attenuation members (first and second attenuation members) 11 and 12 that attenuates the energy of a proton beam that passes through the attenuation members.

First Attenuation Member

The attenuation member 11 corresponds to an attenuation member disclosed in the claims. The attenuation member 11 is disposed on the upstream side of the attenuation member 12 (so as to be close to an inlet of the energy degrader 10) in the traveling direction of a proton beam B. The attenuation member 11 has the shape of a wedge, and includes an incident surface 11a that is a surface perpendicular to the proton beam B and an inclined surface 11b that is formed so as to be inclined with respect to the proton beam B and emits the proton beam B. The attenuation member 11 is formed so as to have different thicknesses in the direction crossing the proton beam B. Meanwhile, the attenuation member 11 may not have the shape of a wedge. The incident surface 11a may be a surface inclined with respect to the proton beam B. Further, an emitting surface may be formed so as to be perpendicular to the proton beam B.

The attenuation member 11 is made of, for example, carbon (C), beryllium (Be), or the like. The attenuation member 11 attenuates the energy of the proton beam B to a different amount of energy according to the incident position of the proton beam B on the attenuation member 11. The proton beam B is decelerated at a deceleration different according to the thickness of the attenuation member 11 through which the proton beam passes, so that the kinetic energy of the proton beam is reduced. Meanwhile, the attenuation member 11 may be made of not a single material but a plurality of different materials. The amount of attenuated energy may be changed by making the proton beam pass through a different material according to the incident position.

Second Attenuation Member

The attenuation member 12 corresponds to a second attenuation member disclosed in the claims. The attenuation member 12 is disposed on the downstream side of the attenuation member 11 (so as to be close to an outlet 13 of the energy degrader 10) in the traveling direction of the proton beam B. The attenuation member 12 has the shape of a wedge, and includes an emission surface 12a that is a surface facing the outlet 13 of the energy degrader 10 and perpendicular to the proton beam B and an inclined surface 12b which is formed so as to be inclined with respect to the proton beam B and where the proton beam B enters. The attenuation member 12 is formed so as to have different thicknesses in the direction crossing the proton beam B. Meanwhile, the attenuation member 12 may not have the shape of a wedge. The emission surface 12a may be a surface inclined with respect to the proton beam B. Further, an incident surface may be formed so as to be perpendicular to the proton beam B.

The attenuation member 12 is made of, for example, carbon (C), beryllium (Be), or the like. The attenuation member 12 attenuates the energy of the proton beam B to a different amount of energy according to the incident position of the proton beam B on the attenuation member 12. The proton beam B is decelerated at a deceleration different according to the thickness of the attenuation member 12 through which the proton beam passes, so that the kinetic energy of the proton beam is reduced. Meanwhile, the attenuation member 12 may be made of not a single material but a plurality of different materials. The amount of attenuated energy may be changed by making the proton beam pass through a different material according to the incident position.

Further, the pair of attenuation members 11 and 12 is disposed so that the inclined surfaces 11b and 12b face each other and the incident surface 11a and the emission surface 12a are parallel to each other. Meanwhile, the inclined surfaces 11b and 12b of the pair of attenuation members 11 and 12 may be disposed parallel to each other and may be disposed at different angles. Further, the attenuation members 11 and 12 may have the same shape, and the shapes of the attenuation members may be different from each other. Furthermore, the energy degrader may further include other attenuation members other than the attenuation members 11 and 12.

Drive of First Attenuation Member

Here, the attenuation member 11 is adapted to be movable in a first axial direction X that is a direction where the amount of attenuated energy of the proton beam B is adjusted and a second axial direction Y that is a direction where the size of the beam diameter of the proton beam B (the width of the beam) is adjusted. The energy degrader 10 includes an energy adjustment drive unit that drives the attenuation member 11 in the first axial direction X in order to change the incident position of the proton beam B on the attenuation member 11, and a beam diameter adjustment drive unit that drives the attenuation member 11 in the second axial direction Y in order to adjust the beam diameter of the proton beam B. That is, the attenuation member 11 is adapted to be capable of being driven in two axial directions, that is, the first and second axial directions X and Y.

Drive of Second Attenuation Member

Further, the attenuation member 12 is adapted to be movable in the first axial direction X where the amount of attenuated energy of the proton beam B is adjusted. The energy degrader 10 includes an energy adjustment drive unit that drives the attenuation member 12 in the first axial direction X in order to change the incident position of the proton beam B on the attenuation member 12. That is, the attenuation member 12 is adapted to be capable of being driven in the first axial direction X.

Controller that Controls the Drive of the Attenuation Members

Figure 3:
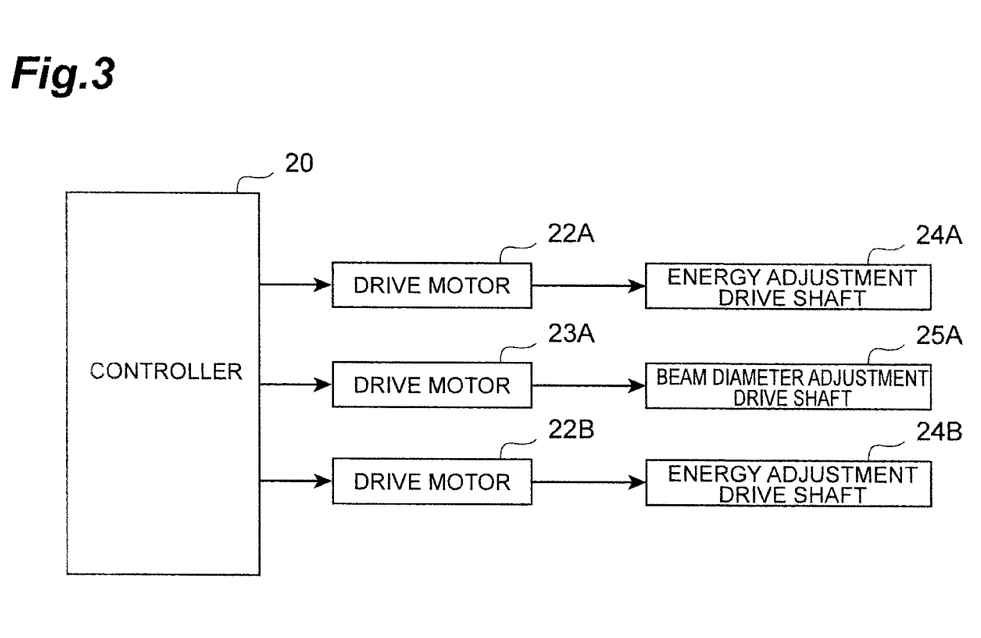
FIG. 3 is a block diagram of a controller that controls the drive of attenuation members.

FIG. 3 is a block diagram of a controller that controls the drive of the attenuation members. The energy degrader 10 includes a controller 20, drive motors 22A, 22B, and 23A, energy adjustment drive shafts 24A and 24B, and a beam diameter adjustment drive shaft 25A.

The controller 20 is assembled in, for example, a proton therapy apparatus control terminal that controls the operation of the particle radiation therapy system 1. The proton therapy apparatus control terminal includes a CPU that performs arithmetic processing, a ROM and a RAM that form a storage unit, an input signal circuit, an output signal circuit, a power circuit, and the like.

The drive motors 22A, 22B, and 23A are electric motors that are operated in accordance with command signals sent from the controller 20. The drive motor 22A applies a drive force to the energy adjustment drive shaft 24A extending in the first axial direction X. Accordingly, a support part supported by the energy adjustment drive shaft 24A is moved in the first axial direction X and moves the attenuation member 11 in the first axial direction X. The drive motor 22B applies a drive force to the energy adjustment drive shaft 24B extending in the first axial direction X. Accordingly, a support part supported by the energy adjustment drive shaft 245 is moved in the first axial direction X and moves the attenuation member 12 in the first axial direction X.

The drive motor 23A applies a drive force to the beam diameter adjustment drive shaft 25A extending in the second axial direction Y. The drive motor 23A and the beam diameter adjustment drive shaft 25A are fixed to the support part provided on the energy adjustment drive shaft 24A, and are moved in the first axial direction X. Further, a support part supported by the beam diameter adjustment drive shaft 25A is moved in the second axial direction Y by a drive force generated from the drive motor 23A, and moves the attenuation member 11 in the second axial direction Y.

Furthermore, the drive motor 22A and the energy adjustment drive shaft 24A function as the energy adjustment drive unit (an energy adjustment drive means) that drives (for driving) the attenuation member 11 in the first axial direction X. The drive motor 22B and the energy adjustment drive shaft 24B function as the energy adjustment drive unit (an energy adjustment drive means that drives (for driving) the attenuation member 12 in the first axial direction X. Meanwhile, the energy adjustment drive shaft 24A and the energy adjustment drive shaft 24B may be the same drive shaft.

Moreover, the drive motor 23A and the beam diameter adjustment drive shaft 25A function as the beam diameter adjustment drive unit (a beam diameter adjustment drive means) that drives (for driving) the attenuation member 11 in the second axial direction Y. Meanwhile, other drive means such as hydraulic cylinders may be used instead of the drive motors. Further, other guide rails or the like may be provided instead of the drive shafts 24A, 24B, and 25A.

Operation of Energy Degrader and Particle Radiation Therapy System

In the particle radiation therapy system 1, a proton beam is accelerated by the cyclotron 2 and the accelerated proton beam is introduced into the energy degrader 10. The proton beam introduced into the energy degrader 10 passes through the attenuation member 11 and the attenuation member 12 in this order. The proton beam passes through the attenuation member 11 and the attenuation member 12 and decelerated, so that the energy of the proton beam is attenuated to a predetermined attenuated amount. Further, the beam diameter of the proton beam B is enlarged according to a gap between the pair of attenuation members 11 and 12, and the beam diameter of the proton beam is enlarged according to a distance between the emission surface 12a of the attenuation member 12 and the outlet 13.

The proton beam B of which the energy has been attenuated by the energy degrader 10 is transported through the transport line 4, and is introduced into the rotating gantry 3. A target portion of a patient is irradiated with the proton beam B that is introduced into the rotating gantry 3. Further, the irradiation depth from the body surface of the patient is adjusted according to the energy of the proton beam B.

FIG. 2B shows a state where the attenuation members 11 and 12 are driven. In the state shown in FIG. 2B, the attenuation members 11 and 12 are disposed so as to be separated from each other in the first and second axial directions X and Y. The attenuation member 11 can be moved in the first and second axial directions X and Y in the energy degrader 10. Furthermore, the attenuation member 12 can be moved in the first axial direction X in the energy degrader 10.

In the state shown in FIG. 2B, the gap between the attenuation members 11 and 12 in the traveling direction of the proton beam B is large in comparison with the state shown in FIG. 2A. Moreover, the attenuation members 11 and 12 are disposed so that the length of the proton beam B, which passes through the inside of the attenuation members 11 and 12, is shortened in the state shown in FIG. 28 in comparison with the state shown in FIG. 2A. While the proton beam B passes through the energy degrader 10, the energy of the proton beam B is attenuated, for example, to 230 MeV from 235 MeV.

According to the energy degrader according to the invention and the particle radiation therapy system including the energy degrader, a plurality of attenuation members 11 and 12 are provided and it is possible to attenuate the energy of the proton beam B entering the attenuation members 11 and 12. In the energy degrader 10, the attenuation member 11 can be driven in the first and second axial directions X and Y. Accordingly, it is possible to adjust the amount of attenuated energy and to adjust the increase of the beam diameter by adjusting the gap between the attenuation members 11 and 12. That is, it is possible to suppress the diffusion of protons in the space between the attenuation members 11 and 12 and to adjust the increase of the beam diameter of the proton beam B by reducing the gap between the attenuation members 11 and 12. Further, when the irradiation of a proton beam B having a large beam diameter is required, it is possible to actively increase the beam diameter by increasing the gap between the attenuation members 11 and 12.

Furthermore, in the energy degrader 10 of this embodiment, it is possible to make the increase of the beam diameter in the space between emission surface 12a and the outlet 13 constant by making a distance between the attenuation member 12 disposed on the downstream side and the outlet 13 of the degrader constant. When a distance between the emission surface 12a and the outlet 13 is previously set so that the increase of the beam diameter becomes minimum, it is possible to adjust the increase of the beam diameter by adjusting only the attenuation member 11 in the Y direction. Meanwhile, when the attenuation member 12 is driven in the Y direction and the attenuation member 12 is moved close to the outlet 13, the distance between the attenuation members 11 and 12 is increased. For this reason, the attenuation member 11 also needs to be moved in the Y direction.

Figure 4:
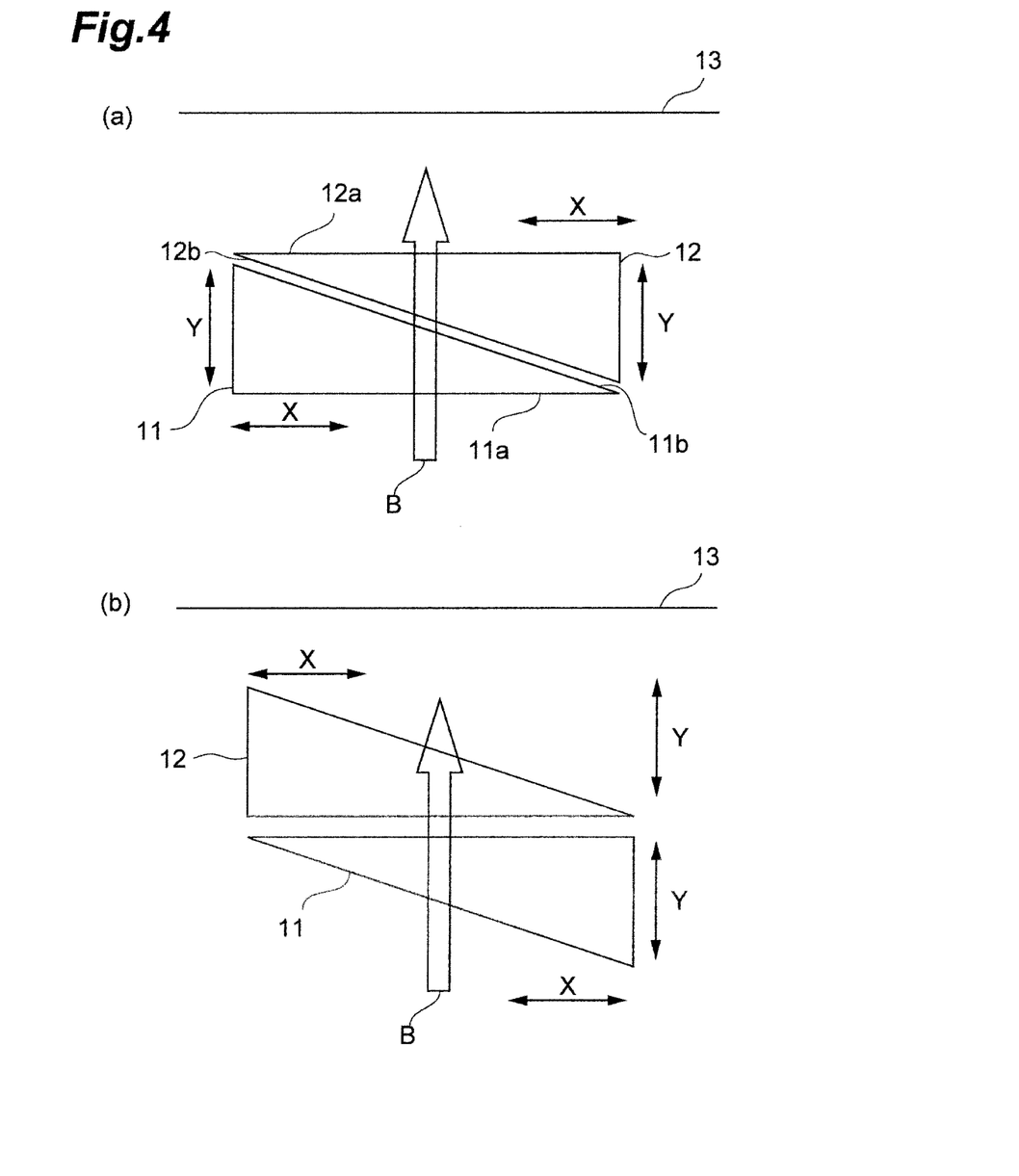
FIG. 4 is a schematic view showing the disposition of attenuation members of an energy degrader according to a modification example.
Figure 5:
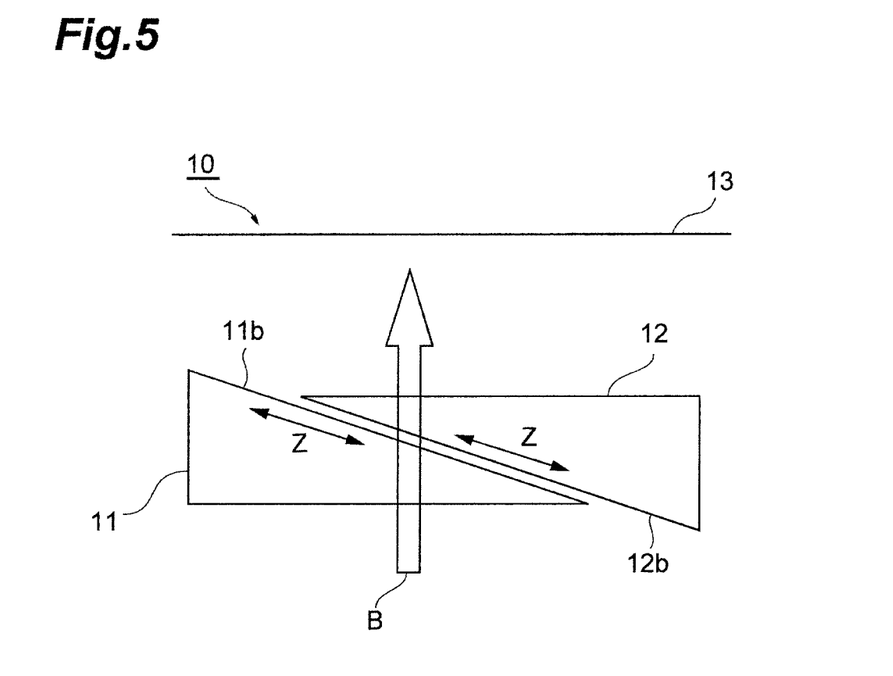
FIG. 5 is a schematic view showing the disposition of attenuation members of an energy degrader according to a modification example.
Figure 6:
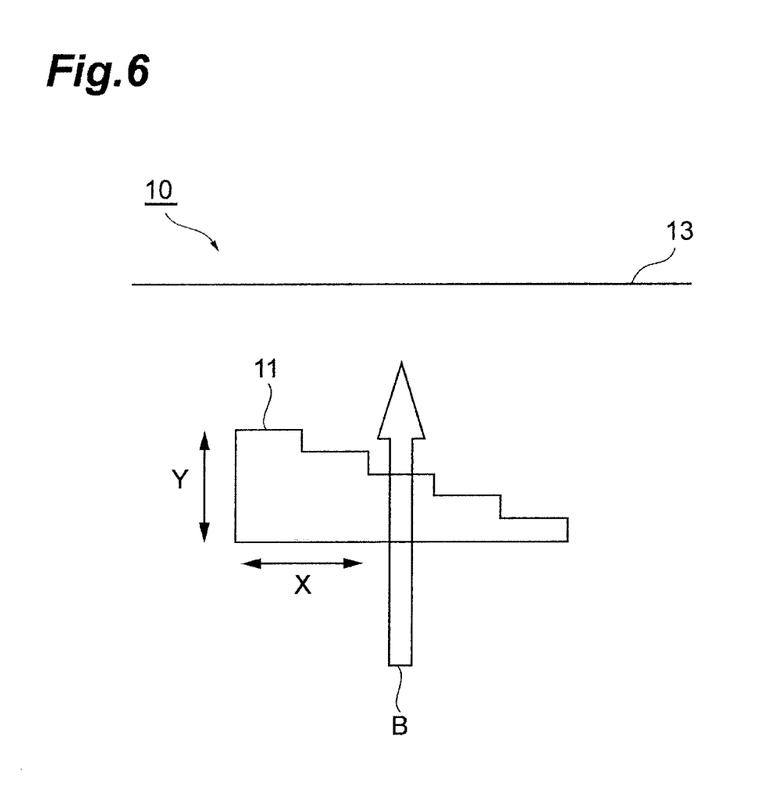
FIG. 6 is a schematic view showing an attenuation member according to a modification example.

The invention has been specifically described above with reference to the embodiment of the invention. However, the invention is not limited to the above-mentioned embodiment. FIGS. 4 and 5 are schematic views showing the disposition of attenuation members of energy degraders according to modification examples, and FIG. 6 is a schematic view showing an attenuation member according to a modification example.

As shown in FIG. 4A, an energy degrader 10 may be adapted to be capable of adjust the beam diameter by moving an attenuation member (second attenuation member) 12 in a second axial direction Y. Accordingly, a gap between the attenuation members 11 and 12 is changed by moving both the attenuation members 11 and 12 in the second axial direction Y, so that it is possible to adjust the increase of the beam diameter.

Further, the attenuation members 11 and 12 may be disposed so that the surfaces of the attenuation members 11 and 12 perpendicular to the proton beam B face each other as shown in FIG. 4B.

Furthermore, an energy degrader 10 may be formed so that attenuation members can be moved along inclined surfaces (third axial direction Z) as shown in FIG. 5. Accordingly, it is possible to adjust the amount of attenuated energy and to adjust the increase of the beam diameter for making a gap between the attenuation members 11 and 12 constant by moving the attenuation members in the third axial direction Z. The pair of attenuation members 11 and 12 may be driven obliquely to the traveling direction of the proton beam B (the Z direction) as shown in FIG. 5, and only one of the attenuation members 11 and 12 may be driven in the Z direction.

Moreover, the shape of the attenuation member is not limited to the shape of a wedge, and may be a shape having a stepped surface as shown in, for example, FIG. 6 instead of the inclined surface. According to the structure including a step-like stepped surface, the attenuation member is disposed so that the proton beam B and the emission surface are perpendicular to each other, and it is possible to adjust the increase of the beam diameter by moving the attenuation member 11 in the Y direction. Further, the energy degrader 10 has included the attenuation members 11 and 12, but may include only the attenuation member 11. Furthermore, in the above-mentioned embodiment, the attenuation member 11 disposed on the upstream side has been adapted to be driven in the Y direction and the attenuation member 12 disposed on the downstream side has been adapted to be driven in the Y direction. However, the attenuation member disposed on the upstream side may be adapted not to be driven in the Y direction and only the attenuation member disposed on the downstream side may be adapted to be driven in the Y direction. In the case of this structure, the attenuation member to be driven in the Y direction corresponds to the attenuation member disclosed in the claims and the attenuation member, which is disposed on the upstream side and is not driven in the Y direction, corresponds to the second attenuation member disclosed in claims.

Further, the energy degrader may be formed so that an attenuation member is rotatable around a predetermined axis extending in the traveling direction of the proton beam B and the attenuation member is movable in the traveling direction of the proton beam B. In this case, the attenuation member is formed so as to have different thicknesses in the rotation direction. Accordingly, it is possible to adjust the amount of attenuated energy by rotating the attenuation member around the predetermined axis and to adjust the increase of the beam diameter by moving the attenuation member in the traveling direction of the beam B.

Furthermore, the disposition of the energy degrader 10 is not limited to the disposition just behind the cyclotron 2, and the energy degrader 10 may be provided in an irradiation nozzle that is installed in the rotating gantry 3.

Moreover, the accelerator is not limited to the cyclotron 2, and other accelerators such as synchrocyclotron may be used.

Figure 7:
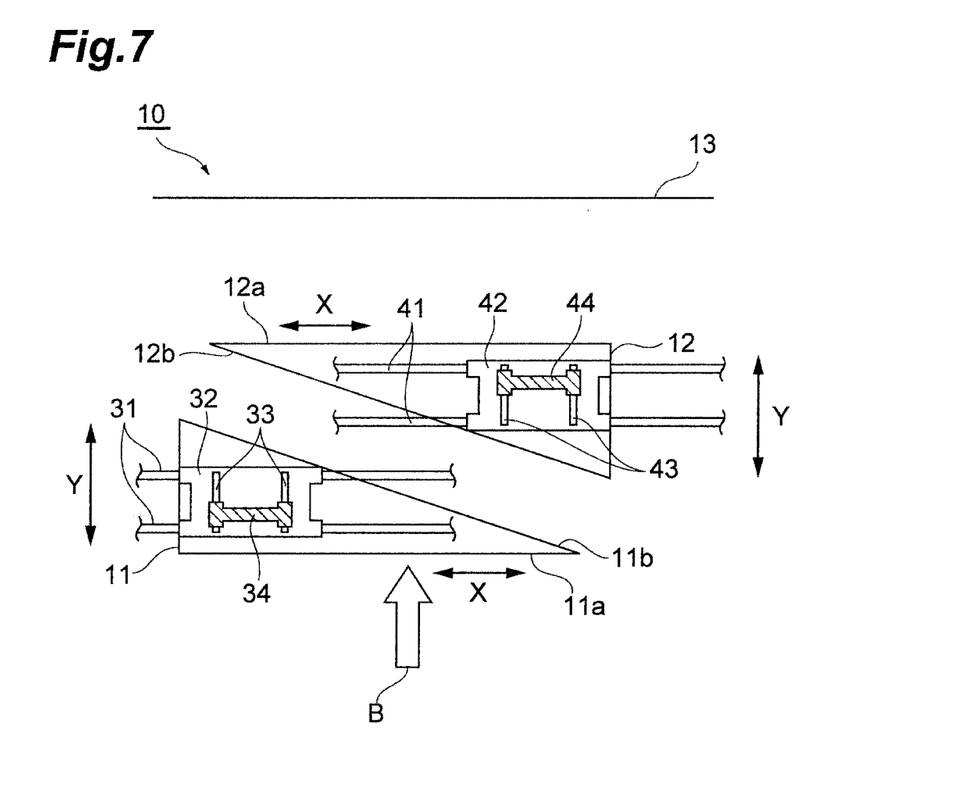
FIG. 7 is a schematic view showing examples of drive mechanisms for attenuation members.

Next, examples of drive unit for the attenuation members 11 and 12 will be described with reference to FIG. 7. A drive unit (energy adjustment drive means and beam diameter adjustment drive means), which moves the attenuation member 11 in the X direction and the Y direction, includes first rails 31 that extend in the X direction, a first stage 32 that is guided by the first rails 31 and is moved in the X direction, second rails 33 that are mounted on the first stage 32 and extend in the Y direction, and a second stage 34 that is guided by the second rails 33 and is moved in the Y direction. The attenuation member 11 is mounted on the second stage 34.

Well-known screw feeding, rollers, linear motors, and the like may be used as a mechanism that moves the first stage 32 along the first rails 31 and a mechanism that moves the second stage 34 along the second rails 33.

Further, when the first stage 32 is moved in the X direction, the second stage 34 and the attenuation member 11 are moved in the X direction. When the second stage 34 is moved in the Y direction, the attenuation member 11 is moved in the Y direction. Accordingly, it is possible to move the attenuation member 11 in the X direction and the Y direction.

Likewise, a drive unit (energy adjustment drive means and beam diameter adjustment drive means), which moves the attenuation member 12 in the X direction and the Y direction, includes first rails 41 that extend in the X direction, a first stage 42 that is guided by the first rails 41 and is moved in the X direction, second rails 43 that are mounted on the first stage 42 and extend in the Y direction, and a second stage 44 that is guided by the second rails 43 and is moved in the Y direction. The attenuation member 12 is mounted on the second stage 44.

Well-known screw feeding, rollers, linear motors, and the like may be used as a mechanism that moves the first stage 42 along the first rails 41 and a mechanism that moves the second stage 44 along the second rails 43.

Further, when the first stage 42 is moved in the X direction, the second stage 44 and the attenuation member 12 are moved in the X direction. When the second stage 44 is moved in the Y direction, the attenuation member 12 is moved in the Y direction. Accordingly, it is possible to move the attenuation member 12 in the X direction and the Y direction.

It should be understood that the invention is not limited to the above-described embodiment, but may be modified into various forms on the basis of the spirit of the invention. Additionally, the modifications are included in the scope of the invention.

FIG. 3

20: CONTROLLER
22A: DRIVE MOTOR
23A: DRIVE MOTOR
22B: DRIVE MOTOR
24A: ENERGY ADJUSTMENT DRIVE SHAFT
25A: BEAM DIAMETER ADJUSTMENT DRIVE SHAFT
24B: ENERGY ADJUSTMENT DRIVE SHAFT

What is claimed is:

1. An energy degrader comprising:
an attenuation member that attenuates energy of entering charged particles to a different amount of energy according to an incident position of the charged particles;
an energy adjustment drive unit that drives the attenuation member in a first axial direction in order to change the incident position of the charged particles; and
a beam diameter adjustment drive unit that drives the attenuation member in a second axial direction different from the first axial direction in order to adjust the beam diameter of the charged particles.

2. The energy degrader according to claim 1, further comprising:
a second attenuation member that is disposed on the upstream or downstream side of the attenuation member in a traveling direction of the charged particles and attenuates energy to a different amount of energy according to incident position of the charged particles; and
a second energy adjustment drive unit that drives the second attenuation member in the first axial direction in order to change the incident position of the charged particles.

3. The energy degrader according to claim 2,
wherein the attenuation member is disposed on the upstream side of the second attenuation member in the traveling direction of the charged particles.

4. A charged particle irradiation system that includes the energy degrader according to claims 1 and performs the irradiation of the charged particles, the charged particle irradiation system comprising:
an accelerator that accelerates the charged particles to be introduced into the energy degrader; and
an irradiation device that performs the irradiation of the charged particles of which energy has been attenuated by the energy degrader.

5. An energy degrader comprising:
an attenuation member that attenuates energy of entering charged particles to a different amount of energy according to an incident position of the charged particles;
energy adjustment drive means for driving the attenuation member in a first axial direction in order to change the incident position of the charged particles; and
beam diameter adjustment drive means for driving the attenuation member in a second axial direction different from the first axial direction in order to adjust the beam diameter of the charged particles.

* * * * *